US006981951B1

(12) United States Patent
Rahe

(10) Patent No.: US 6,981,951 B1
(45) Date of Patent: Jan. 3, 2006

(54) DEVICE FOR RECEIVING AND CONTROLLING VOIDED URINE

(76) Inventor: Martin Rahe, Drosselweg 67, D032609, Huellhorst (DE)

( * ) Notice: Subject to any disclaimer, the term of this patent is extended or adjusted under 35 U.S.C. 154(b) by 0 days.

(21) Appl. No.: 09/936,571

(22) PCT Filed: Feb. 3, 2000

(86) PCT No.: PCT/DE00/00334

§ 371 (c)(1),
(2), (4) Date: Sep. 14, 2001

(87) PCT Pub. No.: WO00/45705

PCT Pub. Date: Aug. 10, 2000

(30) Foreign Application Priority Data

Feb. 4, 1999 (DE) ................................ 199 04 556

(51) Int. Cl.
*A61B 5/00* (2006.01)

(52) U.S. Cl. ...................................................... 600/584

(58) Field of Classification Search ................ 600/573, 600/574, 575, 584; 604/317, 318
See application file for complete search history.

(56) References Cited

U.S. PATENT DOCUMENTS

| | | | | |
|---|---|---|---|---|
| 3,175,553 | A * | 3/1965 | Mattson | 604/318 |
| 4,827,944 | A * | 5/1989 | Nugent | 600/584 |
| 5,042,502 | A * | 8/1991 | Guirguis | 600/584 |
| 5,487,393 | A * | 1/1996 | Haswell et al. | 604/318 |

FOREIGN PATENT DOCUMENTS

| | | |
|---|---|---|
| EP | 0438482 | 7/1991 |
| EP | 0560099 | 9/1993 |

* cited by examiner

*Primary Examiner*—Max F. Hindenburg
(74) *Attorney, Agent, or Firm*—Milde & Hoffberg, LLP

(57) ABSTRACT

Indicators (4) are provided on one side of an indicator carrier (5) for controlling urine which has been caught in a measuring cell (1). The indicators can be perceived through a window (3). The measuring cell (1) is provided with an inlet on the side opposite the window (3). The aim of the invention is to guide urine from the inlet (6) to the indicators 94). To this end, the inventive device has a fluid transport means (9), e.g., blotting paper, which can transport fluid by virtue of the capillarity thereof. A soaking material, e.g., a soaking cushion, can be arranged between the inlet (6) and the indicator carrier (5). Said cushion becomes soaked and locks the inlet (6) when catching urine.

13 Claims, 1 Drawing Sheet

DEVICE FOR RECEIVING AND CONTROLLING VOIDED URINE

BACKGROUND OF THE INVENTION

This invention concerns a device for receiving and examining voided urine and, in particular, urine uncontrollably voided.

A device of this type is already known from the European Patent No. EP 0 560 099 A2. This refers to a coating which wraps and, sometimes, defines the inner space of the device. This coating has at least one passage to let the liquid being examined, urine, flow into the inner part of the device for a pre-determined period of time. Moreover, a device to absorb the liquid, urine, into the inner part of the device as well as a means to stop the flow of the liquid is provided. The composition of the liquid to be examined is determined by means of suitable indicating cards (check-up cards). Because of the limited construction of these cards, their use implies a disadvantage as far as the related reading of the results is concerned, seeing that they cannot be seen from the side of the device bordering with the liquid to be examined.

The European Patent No. EP 0 438 482 B1 also describes a similar device for the absorption and examination of, in this case, uncontrollably voided urine; the device consists of a small measuring cell in the form of an "examination card", which is placed inside a transparent collecting bag, into which the urine flows by means of an inlet tube. The examination card is provided with indicators, to which urine is exposed, to examine the urine collected in terms of developing and existing pathogen infections, which, for example, correspond to the pH, nitrite, leukocyte and electolyte values in the urine. The examination card is covered by a membrane, on the side exposed to the urine, which slows down the urines absorption, causing the urine to penetrate the indicators in a slower manner thus preventing incorrect measurements by reading the high pathogenic concentrations of the urine initially absorbed between the membrane and the indicators. Another swelling material is located which swells after the urine flows into the measuring cell and, by pushing against the membrane, causes the membrane to close after a set period of time. This action counteracts the flushing out of the indicating substances.

In this known measuring cell, the indicators can be observed by means of a transparent external film, acting as a viewing window on the side lying opposite the membrane, because, on the other side, the indicators are covered by the swelling material. This material must lie directly at the rear side of the indicators, so that these can be slowly soaked with urine from the back until a color transfer takes place, which can be seen from the viewing window.

Very good indicators for this known device are available commercially which, due to manufacturing and technical reasons and because of their otherwise different use (as for example direct moisturising with urine to identify disease) are used on synthetic strips that are at least lightly opaque and almost white. When these indicators are used in the known device, they must be placed with their upper surface lying against the swelling material, so that the color transfer can be detected by means of the synthetic strips. However, given the minimal transparency of the material of which the strips are made, the color transfer can not be clearly determined and, in particular, the intensity of the color transfer is difficult to perceive.

SUMMARY OF THE INVENTION

The object of this invention is to improve a known device so that the detection of the color transfer in the indicators and the reliability of the resulting interpretation can be improved in order to allow a clear and reliable determination of the urines composition. Moreover, it must be possible to adjust the device to different fields of application.

This object is achieved, in accordance with the present invention, by providing a device of the type described above having at least one viewing window to which the indicators can be seen, wherein the indicators are arranged on a side bordering the viewing window of an indicator holder, and wherein a liquid transporting means suitable for the transport of liquids due to its capillary action, wraps the indicator holder at the end of the inflow opening and is connected with at least one area of one indicator on one side bordering the viewing window.

Thus, this invention proposes the use of standard indicators arranged on a non-transparent holder and which can be seen through a viewing window in the measuring cell. In order to get the urine from the inflow opening, located on the side opposite the measuring cell, into the indicators, a liquid transporting means is used—foil paper—which, thanks to its capillaries, is suitable for the transport of liquids.

As in the known measuring cell, a swelling material can also be used in this case—a swelling fleece—, which is arranged between the indicator holder and the inflow opening and which swells as a result of the urines absorption and which closes the inflow opening of the measuring cell after a few minutes.

Within the framework of another variation of the device according to the invention, which is used especially in incontinence absorbing means (diapers), a separate swelling cushion is not used and the indicator holder is wrapped with foil paper or a similar capillary material. Here the seal of the system is of secondary importance. In this case, the foil paper first allows the penetration of the liquid into the measuring cell and then, because of the small inflow openings used, the air pressure inside the measuring cell prevents the liquid from penetrating.

The quantity of leukocytes pro volume is determined as follows: The indicators contain indoxylester, which is cleft by means of granulocyte-esterase. It is subsequently possible to determine the quantity of leukocytes pro volume through the granulocyte-esterase concentration. The split product released, indoxyl, reacts with the diosonium salt in the indicators by producing a purple pigment. The color transfer can range between beige and purple, depending on the concentration.

In order to improve the detection of the leukocyte quantity, especially in case of a very small leukocyte concentration, within the framework of the invention, it is proposed to impregnate the used foil paper with indoxylester, in addition to the indicators. In this way more indoxyl is released and a darker hue is obtained due to the higher concentration of indoxylester because of the granulocyte-esterase. A darker color transfer is qualitatively more meaningful and much more stable than a lighter one because the detection is qualitatively improved.

In order to improve the reliability of the system even more, it is also proposed to adopt a more permeable foil paper to prevent the foil paper from retaining the relatively high quantity of leukocytes. The foil paper can be made more permeable by giving it grooves.

It is also proposed to prepare the foil paper with substances which can positively affect the reaction process of the indicators regarding color stabilization, sensitivity, and the foil's features. This prevents changes to the indicators contained in the measuring cell, after a long time (15–20 minutes). In this context, an indicator strip can be replaced with a specifically prepared paper or an additional soaked paper can be integrated into the test strips.

In order to function better, the different indicators need high quantities of test liquid. It is, therefore, proposed to design the conveying band for the test liquid with various widths, in order to control the quantity of the test liquid.

For a full understanding of the present invention, reference should now be made to the following detailed description of the preferred embodiments of the invention as illustrated in the accompanying drawings.

DESCRIPTION OF THE PREFERRED EMBODIMENTS

Figure 1:
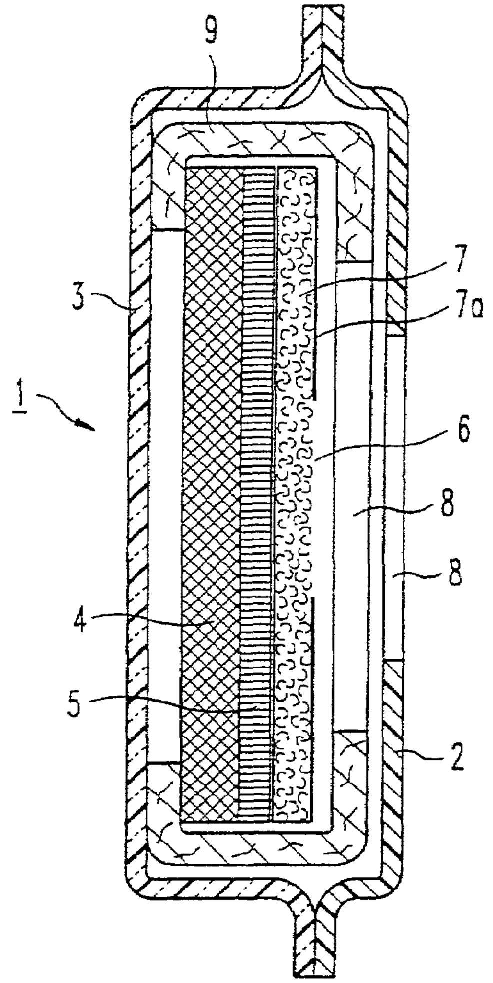
FIG. 1 is a schematic side view of a first embodiment of the device according to the invention.

The preferred embodiments of the present invention will now be described with reference to FIGS. 1–3 of the drawings. Identical elements in the various figures are designated with the same reference numerals.

In FIG. 1, the device for the absorption and the examination of uncontrollably voided urine includes a closed and flat measuring cell 1 preferably made of PP-foil with a rear supporting foil 2 and a front see-through foil creating a transparent area, which works as a viewing window 3. Behind the viewing window 3, the indicators 4 are arranged on an indicator holder 5. One single 1 millimeter wide inflow opening 8 is located on the back support foil.

Moreover, a swelling material in the measuring cell 1 is preferably fitted with a swelling cushion 7, which is lined with a foil 7*a* and fitted with one single 1 millimeter wide inflow opening 6. The inflow openings 6 and 8 are located one directly behind the other.

A liquid transporting means 9, which in this implementation is a foil paper sheet suitable for the transport of liquids due to its capillary action, surrounds the swelling cushion 7, the indicator holder 5 and the indicators 4, in which one edge of the foil paper lies next to the inflow openings 6, 8 and the other edge covers an edge area of all the indicators.

The device works as follows: Through the inflow openings 6, 8, the urine reaches the swelling cushion 7, which swells as a result. In the middle of the capillary foil paper used as the liquid transporting means 9, a small amount of urine is simultaneously absorbed which is transported around the swelling cushion 7 and the transparent indicator holder 5 to the indicators 4. The volume of the swelling cushion 7 increases with the swelling process and, as a result, the measuring cell closes after a few minutes. The capillary foil paper used as a liquid transporting means 9 can obviously be replaced by another means, for example a wick or a suitable liquid transport means not made of cellulose material.

Figure 2:
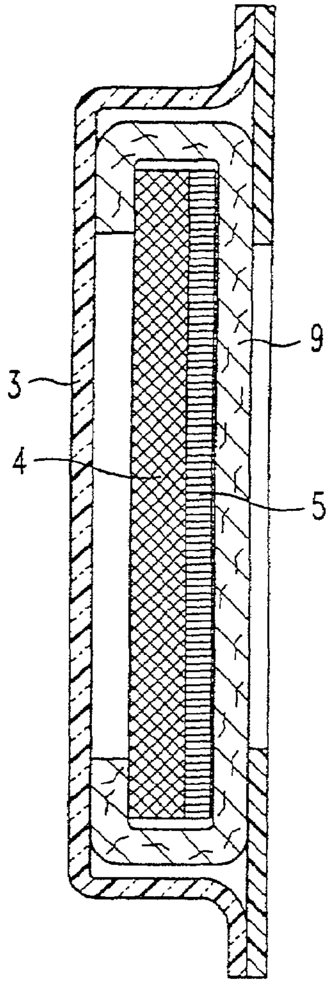
FIG. 2 is a schematic side view of a second embodiment of the device according to the invention.

FIG. 2 shows another variation of the invention, which should be used especially with absorbing incontinence means (diapers). In this case, unlike the implementation described at the beginning, no separate swelling cushion is used because the sealing of the system, in this case, is of secondary importance. The foil paper stretches over another area and wraps the whole rear side of the indicator holder 5. This implementation has a very short reaction time and the indicators need only a small quantity of urine. As a variation to this implementation example embodiment, a swelling cushion can also be used which wraps around the indicator holder and is connected to an edge area of the indicator. In this way the swelling cushion and the liquid transport means are the same thing.

According to the invention, both implementations described can improve the detection of the leukocyte quantity, especially in case of a very small concentration of leukocytes, by using foil paper impregnated with indoxylester. As described at the beginning, the higher concentration of indoxylester causes more indoxyl to be released with a consequent darker and qualitatively more meaningful coloration.

The application of the principle that the foil paper should be prepared with substances which can positively affect the reaction process of the indicators with regard to color stabilization, sensitivity, the features of the foil, can be achieved within the framework of another variation of the invention.

Figure 3:
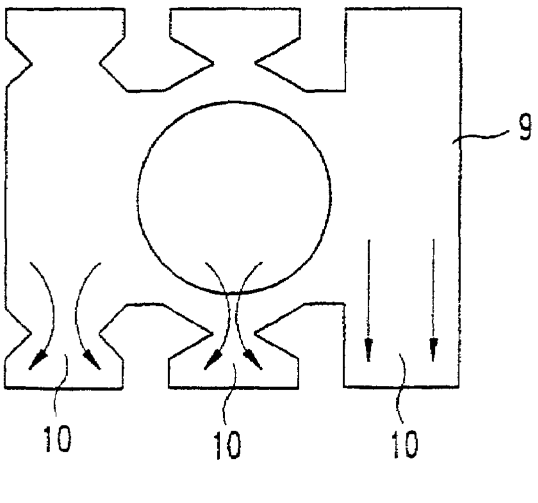
FIG. 3 is a depiction of the foil paper back side according to a preferred embodiment of the invention.

According to FIG. 3, the foil strips 10 of the liquid transporting means 9 have been designed with different widths in order to control the quantity of the test liquid, given that, to ensure better functionality, the various indicators need different quantities of test liquid. For example, the right foil strip is wider than the other two in order to ensure a higher level of reliability and more transparency.

There has thus been shown and described a novel device for receiving and controlling voided urine which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. In a device for the absorption and the examination of voided urine, in the form of a measuring cell, which comprises at least one inflow opening, a plurality of indicators arranged on an indicator holder and at least one viewing window creating a transparent area, through which the indicators can be seen, wherein the indicators are arranged on a side bordering the viewing window of an indicator holder, and wherein a liquid transporting means, suitable for the transport of liquids due to its capillary action, extends from the inflow opening to the indicator holder and is connected with at least one area of one indicator wherein the improvement comprises:

the liquid transporting means wraps the indicator holder and is connected with an area of each indicator on the side bordering the viewing window.

2. The device according to claim 1, wherein a swelling material is placed between the indicator holder and the inflow opening.

3. The device according to claim 2, wherein the swelling material is a swelling cushion made of swelling foil.

4. The device according to claim 3, wherein the swelling cushion is lined with a film and the film is provided with an inflow opening, and wherein the inflow openings, the measuring cell and the swelling cushion are placed directly one behind the other.

5. The device according to claim 1, wherein the liquid transporting means reaches the area of the inflow opening.

6. The device according to claim 1, wherein the liquid transporting means wraps around the back side of the indicator holder.

7. The device according to claim 2, wherein the liquid transporting means is part of the swelling material.

8. The device according to claim 1, wherein the liquid transporting means is foil paper.

9. The device according to claim 1, wherein the liquid transporting means is a material made of non-cellulose material.

10. The device according to claim 1, wherein the liquid transporting means is impregnated with indoxylester to improve the detection of the leukocyte quantity pro volume, such that due to the higher concentration of indoxylester, more indoxyl is released with a consequent darker and qualitatively more meaningful coloration of the indicators.

11. The device according to claim 1, wherein the liquid transporting means is prepared with substances which positively affect a reaction process of the indicators with regard to color stabilization and sensitivity.

12. The device according to claim 1, further comprising conveying bands of different width arranged on the liquid transporting means to control the quantity of the urine in such a way that the various indicators can receive a quantity of test liquid necessary to ensure perfect functionality.

13. The device according to claim 1, wherein the measuring cell is made of PP-foil.

* * * * *